United States Patent [19]

Willis et al.

[11]  4,341,908
[45]  Jul. 27, 1982

[54] AMBRINOL AND ITS HOMOLOGUES

[75] Inventors: Brian J. Willis, Bergenfield; Philip A. Christenson, Midland Park, both of N.J.; Robert A. Mack, Valley Stream, N.Y.

[73] Assignee: Fritzsche Dodge & Olcott Inc., New York, N.Y.

[21] Appl. No.: 161,329

[22] Filed: Jun. 20, 1980

[51] Int. Cl.³ .............................................. C07C 35/23
[52] U.S. Cl. ................................ 568/819; 252/522 R; 568/377; 568/378
[58] Field of Search ............... 568/819, 816, 612, 377, 568/378; 252/522

[56] References Cited

U.S. PATENT DOCUMENTS 3,072,709  1/1963  Saucy ................................. 568/819
3,890,395  6/1975  Jeger et al. ........................ 568/819
4,163,866  8/1979  Strickler ............................ 568/819

FOREIGN PATENT DOCUMENTS 515200  12/1971  Switzerland ........................ 568/819
515987  12/1972  Switzerland ........................ 568/819

Primary Examiner—Werren B. Lone
Attorney, Agent, or Firm—Cooper, Dunham, Clark, Griffin & Moran

[57] ABSTRACT

Compounds useful as fragrance materials having the structure

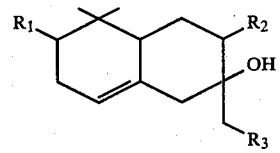

wherein each of $R_1$, $R_2$, and $R_3$ are hydrogen or methyl can be prepared by reacting a halogen-containing cyclohexane, having the structure

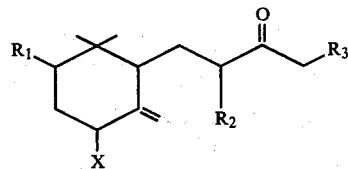

wherein each of $R_1$, $R_2$, and $R_3$ are hydrogen or methyl and X is a halogen, with a reagent capable of effecting intramolecular cyclization.

10 Claims, No Drawings

AMBRINOL AND ITS HOMOLOGUES

BACKGROUND OF THE INVENTION

Copending U.S. application, Ser. No. 129,898, filed Mar. 13, 1980, now U.S. Pat. No. 4,272,412, issued June 9, 1981 the disclosure of which is hereby incorporated by reference into the present application, discloses novel halogen-containing cyclohexane derivatives useful as fragrance materials and their method of preparation. It has now been found that certain of these halogen-containing compounds having the structure

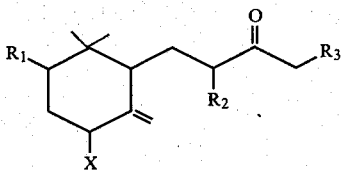

wherein each of $R_1$, $R_2$, and $R_3$ are hydrogen or methyl and X is halogen, are also useful in the preparation of ambrinol and homologues thereof having the structure

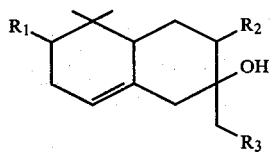

wherein $R_1$, $R_2$, and $R_3$ are as defined above.

Ambrinols are compounds represented by the structure

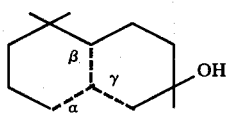

wherein each dashed line represents a carbon-carbon single bond or a carbon-carbon double bond provided that, for any specific compound, two of the three dashed lines represent carbon-carbon single bonds. These compounds are known to exhibit interesting odor properties. Recently, α-ambrinol was shown to be a component of tincture of gray ambergris. (See. B. D. Mookherjee and R. R. Patel, Proceedings of the Seventh International Congress of Essential Oils, Kyoto, Japan, (1977), paper number 136; G. Ohloff et al., Helv. Chim. Acta, (1977), 80, 2763 and 2767; and E. Lederer, et al., Nouveau Journal de Chimie, (1977), 1, 529.)

Ambergris is a concretion formed in the intestinal tract of the cachalot whale. For centuries it has been valued by perfumers for its wet, earthy, musty, seawater-seaweed, tobacco, sandalwood, animal musk, and fecal odor. Presently, ambergris is not readily available, both because of the reduced number of sperm whales and because of efforts to protect those which remain. In fact, some countries prohibit the importation of gray ambergris and other whale products as part of a program to save the whale from extinction. Consequently, efforts have intensified to find commercial synthetic routes to prepare the ambrinols (see U.S. Pat. No. 4,163,866) and other components of ambergris, particularly γ-dihydroionone. (See U.S. Pat. No. 4,129,569).

However, there is no teaching in the prior art which shows or suggests conversion of the halogen-containing cyclohexanes (I) to ambrinol and homologues thereof (II) according to the low cost, efficient process of this invention.

SUMMARY OF THE INVENTION

This invention provides processes for converting novel, halogen-containing cyclohexane compounds, having the structure

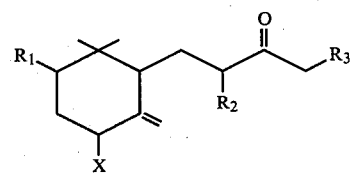

wherein each of $R_1$, $R_2$, and $R_3$ are hydrogen or methyl and wherein X is halogen, to ambrinol and homologues thereof having the structure

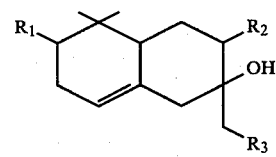

wherein $R_1$, $R_2$, and $R_3$ are as defined above.

One such process involves reacting a halogen-containing cyclohexane intermediate (I) with a reagent capable of effecting intramolecular cyclization to form a bicyclic intermediate, having the structure

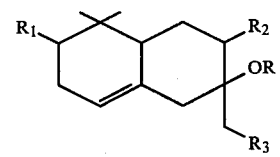

wherein $R_1$, $R_2$, and $R_3$ are as defined above and R is a moiety derived from the reagent used to effect cyclization. Hydrolysis of bicyclic intermediate III yields bicyclic alcohol II.

Alternatively, bicyclic intermediate III may be reacted with an electrophile to form an ester derivative having the structure

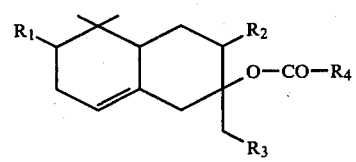

wherein $R_4$ is alkyl or phenyl, or an ether derivative having the structure

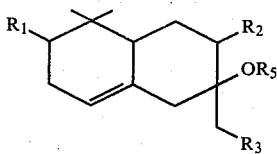

wherein $R_5$ is alkyl or trialkylsilyl. Derivatives IV and V may be used directly as fragrance materials in perfume compositions or may be converted to ambrinol or homologues thereof by standard techniques.

This invention also discloses halogen-containing cyclohexane derivatives I which are useful as fragrance materials and in reactions by which ambrinol and homologues thereof are produced.

DETAILED DESCRIPTION OF THE INVENTION

This invention provides processes for preparing bicyclic alcohols having the structure

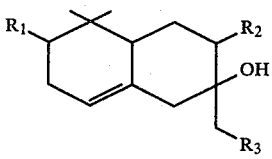

wherein each of $R_1$, $R_2$ and $R_3$ are hydrogen or methyl. Examples of bicyclic alcohols falling within the scope of structural formula II include the following:

1,2,3,4,4a,5,6,7-octahydro-2,5,5-trimethyl-2-naphthalenol;

1,2,3,4,4a,5,6,7-octahydro-2,5,5,6-tetramethyl-2-naphthalenol;

1,2,3,4,4a,5,6,7-octahydro-2,3,5,5-tetramethyl-2-naphthalenol;

1,2,3,4,4a,5,6,7-octahydro-2-ethyl-5,5-dimethyl-2-naphthalenol;

1,2,3,4,4a,5,6,7-octahydro-2,3,5,5,6-pentamethyl-2-naphthalenol;

1,2,3,4,4a,5,6,7-octahydro-2-ethyl-5,5,6-trimethyl-2-naphthalenol;

1,2,3,4,4a,5,6,7-octahydro-2-ethyl-3,5,5-trimethyl-2-naphthalenol; and 1,2,3,4,4a,5,6,7-octahydro-2-ethyl-3,5,5,6-tetramethyl-2-naphthalenol.

These compounds, which are known, have not been prepared previously by the processes described herein.

Compounds II may be prepared by reacting a halogen-containing cyclohexane, having the structure

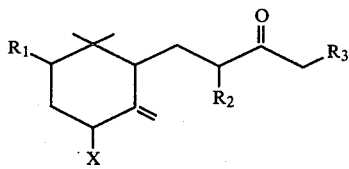

wherein $R_1$, $R_2$ and $R_3$ are as defined above and X is a halogen, such as chlorine, bromine or iodine, with a reagent capable of effecting intramolecular cyclization.

Examples of halogen-containing cyclohexanes falling within the scope of structural formula I include the following:

4-(5-chloro-6-methylene-2,2-dimethylcyclohexyl)-2-butanone;

4-(5-bromo-6-methylene-2,2-dimethylcyclohexyl)-2-butanone;

4-(5-iodo-6-methylene-2,2-dimethylcyclohexyl)-2-butanone;

4-(5-chloro-6-methylene-2,2,3-trimethylcyclohexyl)-2-butanone;

4-(5-bromo-6-methylene-2,2,3-trimethylcyclohexyl)-2-butanone;

4-(5-iodo-6-methylene-2,2,3-trimethylcyclohexyl)-2-butanone;

5-(5-chloro-6-methylene-2,2-dimethylcyclohexyl)-3-pentanone;

5-(5-bromo-6-methylene-2,2-dimethylcyclohexyl)-3-pentanone;

5-(5-chloro-6-methylene-2,2,3-trimethylcyclohexyl)-3-pentanone;

5-(5-bromo-6-methylene-2,2,3-trimethylcyclohexyl)-3-pentanone;

4-(5-chloro-6-methylene-2,2-dimethylcyclohexyl)-3-methyl-2-butanone;

4-(5-bromo-6-methylene-2,2-dimethylcyclohexyl)-3-methyl-2-butanone;

4-(5-chloro-6-methylene-2,2,3-trimethylcyclohexyl)-3-methyl-2-butanone;

4-(5-bromo-6-methylene-2,2,3-trimethylcyclohexyl)-3-methyl-2-butanone;

5-(5-chloro-6-methylene-2,2-dimethylcyclohexyl)-4-methyl-3-pentanone;

5-(5-bromo-6-methylene-2,2-dimethylcyclohexyl)-4-methyl-3-pentanone;

5-(5-chloro-6-methylene-2,2,3-trimethylcyclohexyl)-4-methyl-3-pentanone; and 5-(5-bromo-6-methylene-2,2,3-trimethylcyclohexyl)-4-methyl-3-pentanone.

A wide variety of reagents are useful for effecting intramolecular cyclization of the halogen-containing cyclohexane I to produce bicyclic intermediate III and bicyclic alcohol II. These include metals from Groups 1 and 2 of the Periodic Table, e.g., Li, Mg, Ca and Zn; electron transfer reagents such as Na/naphthalene; alloys including amalgams of Groups 1, 2 and 3 elements, e.g., Li, Na, K, Ca and Al, and Transition metals such as Fe, Cu, Cd and Hg; salts of elements of Groups 1, 2 and 3 of the Periodic Table and salts of Transition metals such as $Zn^{2+}$, $Cu^{2+}$, $Hg^{2+}$, $Cr^{2+}$, $V^{2+}$ and $Ti^{3+}$. In addition, it will be apparent to one skilled in the art that numerous additional reagents may be useful in effecting conversion of compound I to compound II.

The cyclization reaction may be carried out at temperatures in the range from about $-20°$ to about $160°$ C. Preferably, the reaction is carried out at a temperature in the range from about $0°$ to about $+120°$ C.

The amount of reagent employed in the reaction may vary widely depending upon the precise reagent and cyclohexane employed as well as the conditions under which the reaction is carried out.

A variety of solvent systems are useful for the cyclization reaction. Thus, for example, bicyclic alcohol II may be formed directly in protic solvents or solvent systems, such as methanol, ethanol, acetic acid, or solvent systems such as tetrahydrofuran/water, tetrahydrofuran/acetic acid, or methanol/water. Bicyclic intermediates having the structure

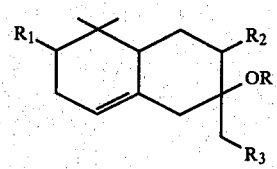

wherein $R_1$, $R_2$ and $R_3$ are as defined above and R is a moiety derived from the reagent used to effect cyclization, may be formed in non-protic solvents such as diethyl ether, tetrahydrofuran, benzene, toluene, dimethylformamide, and dimethylsulfoxide, or solvent systems such as tetrahydrofuran/toluene or benzene/dimethylformamide. Hydrolysis of intermediate III yields alcohol II.

Alternatively, bicyclic intermediates III may be treated with an electrophile to produce esters or ethers. Thus, esterification with an acid anhydride having the general formula $(R_4CO)_2O$, e.g., acetic anhydride, or an acid chloride having the general formula $(R_4COX)$, e.g., $C_6H_5COCl$, provides a bicyclic ester having the structure

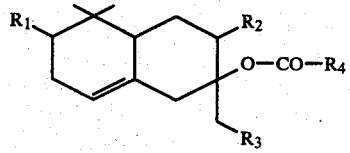

wherein $R_4$ may be alkyl, particularly lower alkyl, e.g. $C_1$ to $C_6$ alkyl, or phenyl.

Etherification with an alkyl halide having the general formula $R_5X$, e.g., $CH_3I$, a trialkylsilyl halide having the general formula $(R_5)_3SiX$, e.g., $Me_3SiCl$, or an alkyl sulfate having the general formula $(R_5)_2SO_4$, e.g., $Me_2SO_4$, provides a bicyclic ether having the structure

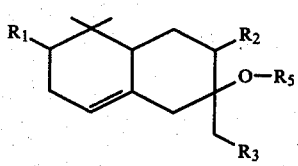

wherein $R_5$ is alkyl, particularly lower alkyl, e.g. $C_1$ to $C_6$ alkyl, or phenyl or trialkylsilyl.

Bicyclic esters IV and bicyclic ethers V then may be hydrolyzed to produce bicyclic alcohols II by standard techniques. (See, for example, J. F. W. McOmie, *Protective Groups in Organic Chemistry*, Plenum Publishing Co., page 95 (1973)).

Recovery and purification of the final products is achieved by conventional techniques which include extraction, distillation, crystallization, preparative chromatographic separation, and the like.

The foregoing structural formulae are intended to embrace the various individual stereoisomers as well as mixtures. Accordingly, it is to be understood that such structural formulae include both the individual stereoisomers and mixtures thereof.

The bicyclic esters IV and the bicyclic ethers V of this invention may be employed singly or in combination to impart novel characteristics to fragrance compositions. They may be incorporated into fragrance compositions for use in detergents, soaps, perfumes, bath preparations, cosmetic preparations and the like. When so employed, the compound or compounds should desirably be present in amounts from about 0.1% to about 80% by weight based upon the weight of the composition.

A number of examples are now provided to more fully illustrate the practice of this invention. However, these examples are in no way meant to limit its scope.

The following instrumentation was used to characterize the compounds. Nuclear Magnetic Resonance (NMR) spectra were recorded with a Varian Associates T-60A spectrometer using tetramethylsilane as the internal reference. Infrared (IR) spectra were obtained with a Perkin Elmer 710 B spectrophotometer. Mass spectra (MS) were obtained with a Hewlett-Packard 5985 Mass Spectrometer. Unless otherwise stated, weights are in grams, temperatures are in degrees centigrade, and pressures in mm Hg.

EXAMPLE 1

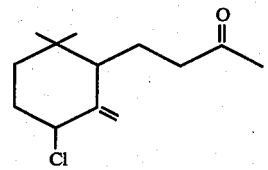

To a mixture of commercial bleach (28.5 ml of a 5.25% solution of sodium hypochlorite), α-dihydroionone (3.88 g) and methylene chloride (110 ml), a solution of potassium phosphate (monobasic) (5.44 g) in water (40 ml) was added during a 15 minute period. The resulting mixture was stirred for 1 hour at 25°. The methylene chloride solution was washed with sodium bicarbonate solution, the solvent evaporated, and the residue distilled to give 2.81 g (61% yield) of 4-(5-chloro-6-methylene-2,2-dimethylcyclohexyl)-2-butanone, bp 101°–106°, 0.2 mm. NMR (CDCl$_3$) δ0.85 and 0.95 (6H, 2 s, >C(CH$_3$)$_2$), 0.9–2.6 (9H, m), 2.10 (3H, s, —COCH$_3$), 4.36–4.55 (1H, t, J=6 Hz,>CHCl), 4.76 and 5.33 (2H, 2 s, >C=(CH$_2$)). IR (film), γmax 2950, 1720, 1675, 1650, 1455, 1360 cm$^{-1}$. MS m/e 193, 175, 159, 134, 119.

EXAMPLE 2

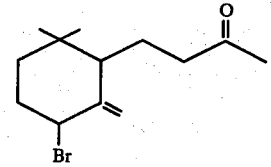

A solution of sodium bromide (6.17 g) in water (10 ml) and commercial bleach (31.2 ml of a solution of sodium hypochlorite) were stirred together for 5 minutes, and a solution of dihydro-α-ionone (3.88 g) in methylene chloride was added. Then, a solution of potassium phosphate (monobasic) (5.44 g) in water (30 ml) was added during 30 minutes. After stirring for 50 minutes at 25°, a solution of sodium bromide (2.05 g) and commercial bleach (10 ml) was added, followed by a solution of potassium phosphate (monobasic) (2.72 g) in water (10 ml) and the reaction mixture stirred for 15 minutes at 25°. The methylene chloride solution was washed with sodium bicarbonate solution and the solvent evaporated to provide the crude product (5.86 g). Column chromatography gave 1.87 g of 4-(5-bromo-6-methylene-2,2-dimethylcyclohexyl)-2-butanone. NMR (CDCl₃) δ0.93 (6H, s, >C(CH₃)₂), 0.9-2.6 (9H, m), 2.12 (3H, s, —COCH₃), 4.6-5.1 (1H, m, >CHBr), 4.76 and 5.28 (2H, 2 s, >C=CH₂), 4.68 and 5.20 (2H, 2 s, >C=CH₂, minor isomer; isomer ratio 3/1). IR (film) γmax 2960, 1720, 1675, 1650, 1455, 1360 cm⁻¹.

EXAMPLE 3

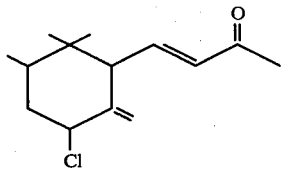

To a mixture of commercial bleach (42.6 ml of a 5.25% solution of sodium hypochlorite), α-irone (6.24 g), and methylene chloride (200 ml), a solution of potassium phosphate (monobasic) (8.16 g) in water (40 ml) was added during a 30 minute period. The resulting mixture was stirred for 1 h at 25°. The methylene chloride solution was washed with sodium bicarbonate solution and evaporated to give 7.3 g of crude product. Purification by column chromatography gave 4.59 g of 4-(5-chloro-6-methylene-2,2,3-trimethylcyclohexyl)-3-buten-2-one. NMR (CDCl₃) δ0.70-0.78 (2H, d, J=5 Hz, >CHCH₃), 0.90, 0.93 and 0.99 (6H, 3 s, >C(CH₃)₂), 0.9-1.3 (1H, m, >CHCH₃), 1.5-2.1 (2H, m, —CH₂—), 2.25, 2.26 and 2.28 (3H, 3 s, —COCH₃), 2.67 and 2.83 (1H, 2 s, >CH-CH=CH—), 4.6-4.9 (1H, m, >CHCl), 4.93 and 5.12 (2H, 2 s, >C=CH₂), 5.8-6.3 (1H, m, -CH=CH-CO-), 6.6-7.6 (1H, m, -CH=CHCO—). IR (film) γmax 2960, 1695, 1675, 1620, 1460, 1430 cm⁻¹. MS m/e 207, 163.

EXAMPLE 4

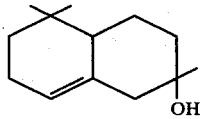

To a suspension of magnesium (14.58 g) and mercuric chloride (4.5 g) in tetrahydrofuran (20 ml) at 20°-25°, a solution of 4-(5-chloro-6-methylene-2,2-dimethylcyclohexyl)-2-butanone (45.8 g) in tetrahydrofuran (500 ml) was added over a 2 h period. The resulting mixture was stirred for 1 h at 25°. Saturated ammonium chloride solution (100 ml) was added, and the mixture was diluted with water. The organic products were extracted with ether and the combined organic layers were washed with sodium bicarbonate solution. The solvent was evaporated to give 42.4 g of crude α-ambrinol which by instrumental analysis contained 8% of 2,6,6-trimethyl-9-methylenebicyclo[3.3.1]nonan-2-ol, and 67% of α-ambrinol. Distillation of the crude product gave 22.76 g (59%) of α-ambrinol as a mixture of stereoisomers, bp 82°-110°, 0.2 mm. The stereoisomers were separated by chromatography. Major isomer: 1,2,3,4,4aβ,5,6,7-octahydro-2β,5,5-trimethyl-2α-naphthalenol; NMR (CDCl₃) δ0.87 and 0.92 (6H, 2 s, >C(CH₃)₂), 1.22 (3H, s, >C(CH₃)OH), 0.9-2.2 (12H, m), 5.30-5.60 (1H, m, -CH=C<). IR (film) νmax 3450, 2940, 1455, 1380, 1360 cm⁻¹. MS m/e 194, 176, 161, 136. Minor isomer: 1,2,3,4,4aβ,5,6,7-octahydro-2α,5,5-trimethyl-2β-naphthalenol, mp 75°-78°; NMR (CDCl₃) δ0.82 and 0.93 (6H, 2 s, >C(CH₃)₂), 1.12 (3H, s, >C(CH₃)OH), 0.9-2.2 (12H, m), 5.20-5.47 (1H, m, -CH=C<). IR (CCl₄) γmax 3590, 3325, 2900, 1675, 1450, 1380, 1370, 1360 cm⁻¹. MS m/e 176, 161, 136.

EXAMPLE 5

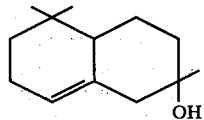

A suspension of magnesium (2.62 g) and mercuric chloride (0.87 g) in tetrahydrofuran (10 ml) was reacted with a solution of 4-(5-chloro-6-methylene-2,2,3-trimethylcyclohexyl)-2-butanone (8.71 g) in tetrahydrofuran (180 ml) as described in Example 4 to give, after chromatography, 2.42 g (32%) of 1,2,3,4,4aβ,5,6,7-octahydro-2β,5,5,6-tetramethyl-2α-naphthalenol. (NMR (CDCl₃) δ0.76-0.86 (3H, d, J=6 Hz, >CHCH₃), 0.79 and 0.85 (6H, 2 s, >C(CH₃)₂), 1.22 (3H, s, >C(CH₃)OH), 0.8-2.2 (11H,m), 5.25-5.75 (1H, m, -CH=C<); IR (film) γmax 3595, 3460, 2960, 1670, 1450, 1382, 1370 cm⁻¹; MS m/e 208, 190, 175, 145), and 0.56 g (8%) of 1,2,3,4,4aβ,5,6,7-octahydro-2α,5,5,6-tetramethyl-2β-naphthalenol, mp 73°-77° (NMR (CDCl₃) δ0.75-0.85 (3H, d, J=6 Hz, >CHCH₃, 0.82 and 0.85 (6H, 2 s, >C(CH₃)₂), 1.12 (3H, s, >C(CH₃)OH), 0.8-2.2 (11H, m), 5.15-5.34 (1H, m, -CH=C<); IR (CCl₄) γmax 3595, 3350, 2960, 1670, 1460, 1385, 1370, 1360 cm⁻¹; MS m/e 190, 175, 161, 145).

EXAMPLE 6

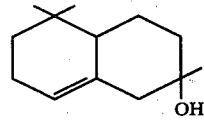

Magnesium (0.068 g) and mercuric chloride (0.010 g) in tetrahydrofuran (1 ml) was reacted with 4-(5-bromo-6-methylene-2,2-dimethylcyclohexyl)-2-butanone (0.254 g) in tetrahydrofuran (8 ml) as described above. Work-up gave 0.162 g of crude α-ambrinol, which by instrumental analysis contained 11% of 2,6,6-trimethyl-9-methylenebicyclo[3.3.1]nonan-2-ol and 76% α-ambrinol.

EXAMPLE 7

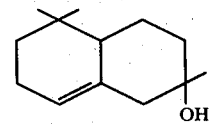

To a suspension of calcium turnings (0.60 g) and mercuric chloride (0.075 g) in tetrahydrofuran (1 ml), a solution of 4-(5-chloro-6-methylene-2,2-dimethylcyclohexyl)-2-butanone (1.14 g) in tetrahydrofuran (10 ml) was added over a 1 h period at 60°-65°. The resulting mixture was heated at 60°–65° for a further 1 h, then cooled to 0°, and saturated ammonium chloride solution was added. Work-up and Kugelrohr distillation gave 0.485 g (50%) of crude product, which by instrumental analysis contained 59% of α-ambrinol and 5% of 2,6,6-trimethyl-9-methylenebicyclo [3.3.1]nonan-2-ol.

EXAMPLE 8

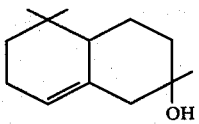

A mixture of zinc dust (2.0 g), 4-(5-chloro-6-methylene-2,2-dimethylcyclohexyl)-2-butanone (0.686 g) and acetic acid (15 ml) was stirred at 20°–25° for 17 h. The mixture was filtered, the filtrate diluted with hexanes (50 ml), and washed with water, and sodium bicarbonate solution. The solvents were evaporated and the residue Kugelrohr distilled to give 0.542 g of crude product, which by instrumental analysis contained 41% of α-ambrinol and 23% of 2,6,6-trimethyl-9-methylenebicyclo[3.3.1]nonan-2-ol.

EXAMPLE 9

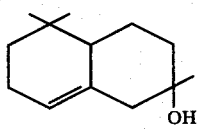

To a suspension of chromium trichloride (0.950 g) in tetrahydrofuran (5 ml) at 25° lithium aluminum hydride (0.114 g) was added portionwise. A solution of 4-(5-chloro-6-methylene-2,2-dimethylcyclohexyl)-2-butanone (0.686 g) in tetrahydrofuran (15 ml) was then added dropwise to the reaction mixture during a 1 h period at 25°. The resulting mixture was stirred for 2 h at 25°, then heated for 1 h at 60°–65°, and finally the mixture was cooled, poured into water, and extracted with hexanes. The organic extracts were washed with sodium bicarbonate solution, the solvents were evaporated, and the residue Kugelrohr distilled to give 0.391 g (67%) of product, which by instrumental analysis contained 29% of α-ambrinol and 44% of 2,6,6-trimethyl-9-methylenebicyclo[3.3.1]nonan-2-ol.

EXAMPLE 10

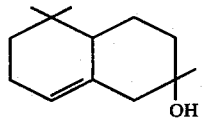

Sodium (0.23 g) was added to a solution of naphthalene (2.56 g) in tetrahydrofuran (15 ml). A solution of 4-(5-chloro-6-methylene-2,2-dimethylcyclohexyl)-2-butanone (1.14 g) in tetrahydrofuran (10 ml) was added to the reaction mixture during a 1 h period at 25°. The resulting mixture was stirred at 25° for 30 min., and then methanol (5 ml) was added. The mixture was poured into water (50 ml), acidified with 6 N HCl, and extracted with hexanes. The organic extracts were washed with water and sodium bicarbonate solution. Evaporation of solvents and chromatography of the residue gave 0.132 g (14%) of α-ambrinol, which by instrumental anlaysis was identical with that described in Example 4.

EXAMPLE 11

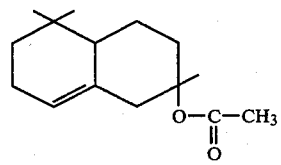

To a suspension of magnesium (1.07 g) and mercuric chloride (0.33 g) in tetrahydrofuran (5 ml) at 20°–25°, a solution of 4-(5-chloro-6-methylene-2,2-dimethylcyclohexyl)-2-butanone (3.42 g) in tetrahydrofuran (55 ml) was added over a 2 h period. The mixture was stirred for 1 h at 25°, acetic anhydride (1.84 g) was added, and the mixture was stirred at 25° for 18 h, and then at 60°–65° for 3 h. The cooled mixture was poured onto ice water and the organic products extracted with hexane. The combined organic extracts were washed with sodium bicarbonate solution and the solvent evaporated to give 2.45 g of crude product. Chromatography gave 1,2,3,4,4a,5,6,7-octahydro-2-acetoxy-2,5,5-trimethylnaphthalene 1.62 g (46%) as a mixture of stereoisomers. NMR (CDCl$_3$) δ0.83, 0.93 and 0.98 (6H, 3 s, >C(CH$_3$)$_2$), 1.40 and 1.47 (3H, 2 s, ratio; 2:3, >C(CH$_3$)O—), 1.92 and 1.97 (3H, 2 s, ratio; 3:2, CH$_3$CO$_2$—), 0.8–2.4 (11H, m) 5.25–5.55 (1H, m, -CH=C<). IR (film) γmax 2940, 1735, 1445, 1365 cm$^{-1}$. MS m/e 176, 161, 120.

EXAMPLE 12

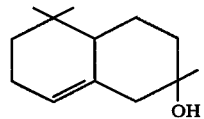

A mixture of 1,2,3,4,4a,5,6,7-octahydro-2-acetoxy-2,5,5-trimethylnaphthalene (0.75 g), potassium hydroxide (2.09 g), water (5 ml) and methanol (30 ml) was refluxed for 3 h. Water (60 ml) was added to the cooled reaction mixture, and the organic products extracted with ether. The ether extracts were washed sequentially with 6 N hydrochloric acid, water, and sodium bicarbonate solution. The solvent was evaporated and the residue distilled to give 0.50 g (81%) of α-ambrinol. Spectral and analytical data for this material was consistent with that given in Example 4.

EXAMPLE 13

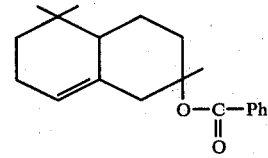

A mixture of magnesium (1.07 g) and mercuric chloride (0.33 g) was reacted with 4-(5-chloro-6-methylene-2,2-dimethylcyclohexyl)-2-butanone (3.42 g) in tetrahydrofuran (60 ml), and the intermediate reacted with benzoic anyhydride (4.07 g) according to the procedure described in Example 11. Work-up and chromatography gave 1,2,3,4,4a,5,6,7-octahydro-2-benzoyloxy-2,5,5-trimethylnaphthalene, 1.64 g (37%, 75% pure), as a mixture of stereoisomers. NMR (CDCl₃) δ0.77, 0.84 and 0.93 (6H, 3 s, >C(CH₃)₂), 1.53 and 1.60 (3H, 2 s, ratio; 35:65, >C(CH₃)O—), 0.8-2.4 (11H, m) 5.25-5.58 (1H, m, —CH=C<), 7.20-8.25 (5H, m, C₆H₅CO₂—). IR (film) γmax 2940, 1715, 1600, 1585, 1450 cm⁻¹. MS m/e 176, 161, 120, 105. This benzoate may be converted to α-ambrinol by a method similar to that described in Example 12.

EXAMPLE 14

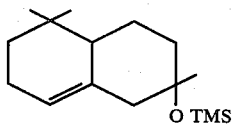

To a suspension of magnesium (1.07 g) and mercuric chloride (0.33 g) in tetrahydrofuran (5 ml) at 20°-25°, a solution of 4-(5-chloro-6-methylene-2,2-dimethylcyclohexyl)-2-butanone (3.42 g) in tetrahydrofuran (55 ml) was added over a 2 h period. The resulting mixture was stirred for 1 h at 25°, chlorotrimethylsilane (4.6 ml) was added, and the mixture was stirred at 25° for 18 h, and then at 60°-65° for 8 h. The cooled mixture was diluted with hexanes and poured onto water. The organic layer was washed with sodium bicarbonate solution and the solvent evaporated to give 2.80 g of crude product. Chromatography gave 1,2,3,4,4a,5,6,7-octahydro-2-trimethylsilyloxy-2,5,5-trimethylnaphthalene, 0.93 g (23%, 83% pure) as a mixture of stereoisomers. NMR (CDCl₃) δ0.08 (9H, s, —Si(CH₃)₃), 0.81 and 0.93 (6H, 2 s, >C(CH₃)₂), 1.22 (3H, s, >C(CH₃)O—), 0.8-2.3 (11H, m), 5.20-5.45 (1H, m, —CH=C<). IR (film) γmax 2950, 1665, 1450, 1385, 1375, 1370 cm⁻¹. MS m/e 176, 161, 143, 120.

EXAMPLE 15

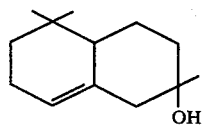

A mixture of 1,2,3,4,4a,5,6,7-octahydro-2-trimethylsilyloxy-2,5,5-trimethylnaphthalene (0.78 g), ethanol (40 ml), water (4 ml) and 2 N hydrochloric acid (1 ml) was stirred at 20°-25° for 17 h. The mixture was poured onto water and extracted with hexanes. The combined organic extracts were washed with sodium bicarbonate solution and the solvent evaporated to give 0.61 g of crude product. Chromatography gave 0.42 g (75%) of α-ambrinol. Spectral and analytical data for this material was consistent with that given in Example 4.

EXAMPLE 16

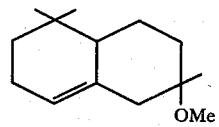

A mixture of sodium hydride (0.414 g), α-ambrinol (2.91 g), hexamethylphosphoric triamide (5 ml) and tetrahydrofuran (40 ml) was heated at 60°-65° for 2 h. The mixture was cooled to 25° and methyl iodide (4.7 ml) was added. After stirring the reaction mixture at 25° for 17 h, additional methyl iodide (2 ml) was added. The mixture was heated at 40° for 2 h, cooled to 25° and methanol (5 ml) added. The mixture was poured into water and extracted with hexanes. The organic extracts were washed with water and the solvents evaporated. The residue was chromatographed to give 1.92 g (62%) of 1,2,3,4,4a,5,6,7-octahydro-2-methyoxy-2,5,5-trimethyl-yl-naphthalene as a mixture of stereoisomers. NMR (CDCl₃) δ0.81 and 0.91 (6 H, 2s, >C(CH₃)₂), 1.02 and 1.04 (3H, 2 s, ratio; 4:1>C(CH₃)OCH₃), 0.8-2.3 (11H, m), 3.10 and 3.21 (3 H, 2s, ratio; 4:1 —OCH₃), 5.2-5.4 (1H, m, —CH=C<). IR (film) γmax 2910, 1665, 1450, 1375, 1360 cm⁻¹. MS (major isomer) m/e 208, 176, 161, 133, 85; (minor isomer) m/e 176, 161, 133, 85).

EXAMPLE 17

A fantasy floral perfume composition may be prepared by mixing the following:

|  | % |
| --- | --- |
| Musk Ketone | 2.0 |
| Coumarin | 1.0 |
| Methyl everninate | 1.0 |
| Geraniol | 10.0 |
| Phenylethyl alcohol | 16.0 |
| Citronellol | 2.0 |
| Geranyl acetate | 1.0 |
| Indole 10% | 1.0 |
| Rose Otto | 3.0 |
| Rose Oxide 10% | 1.0 |
| Hydroxycitronellal | 11.0 |
| Dihydrocelamone FDO | 13.0 |
| Hexyl cinnamic aldehyde | 10.0 |
| Benzyl acetate | 1.0 |
| Oil Ylang extra | 0.5 |
| Phenylethyl acetate | 1.0 |
| Gamma undecalactone 10% | 1.0 |
| Methylionone gamma | 4.5 |
| Cedroxyde | 4.0 |
| Oil Vetiver Reunion | 3.0 |
| Oil Bergamot rectified | 3.0 |
| 1,2,3,4,4a,5,6,7-octahydro-2-acetoxy-2,5,5-trimethylnaphthalene | 10.0 |
|  | 100.0 |

EXAMPLE 18

A fantasy woody perfume composition may be prepared by mixing the following:

|  | % |
| --- | --- |
| Rhodinol Extra | 7.0 |
| Phenylethyl phenylacetate | 11.0 |
| Phenylethyl alcohol | 10.0 |
| Oil Rose Bulgarian | 5.0 |
| Oil Ylang Extra | 4.0 |
| Jasmin Absolute | 3.0 |

-continued

|  | % |
|---|---|
| Linalool | 6.0 |
| Oil Vetiver Reunion | 12.0 |
| Santol FDO | 5.0 |
| Musk ketone | 10.0 |
| Coumarin | 4.0 |
| Amyl cinnamic aldehyde | 3.0 |
| Hydroxycitronellal | 13.0 |
| 1,2,3,4,4a,5,6,7-octahydro-2-methoxy-2,5,5-trimethylnaphthalene | 7.0 |
|  | 100.0 |

As will be obvious to one skilled in the art, many modifications, variations, and alterations can be made in the practices of this invention without departing from the spirit and scope thereof as set forth in the claims which follow.

What is claimed is:

1. A method of preparing a bicyclic alcohol having the structure

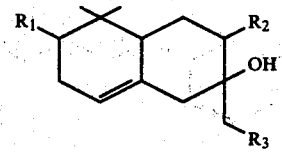

wherein each of $R_1$, $R_2$ and $R_3$ are hydrogen or methyl which comprises reacting under suitable conditions a halogen-containing cyclohexane having the structure

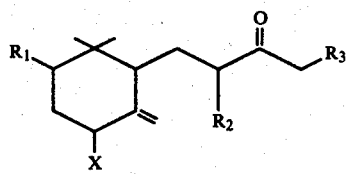

wherein each of $R_1$, $R_2$ and $R_3$ are hydrogen or methyl and X is a halogen with a reagent capable of effecting intramolecular cyclization of said halogen-containing cyclohexane compound and selected from the group consisting of metals from Groups 1 and 2 of the Periodic Table; electron transfer reagents such as Na/napthalene; alloys including amalgams of Group 1, 2 and 3 elements; Transition metals such as Fe, Cu, Cd and Hg; salts of elements of Groups 1, 2 and 3 of the Periodic Table; and salts of Transition metals such as $Zn^{2+}$, $Cu^{2+}$, $Hg^{2+}$, $Cr^{2+}$, $V^{2+}$ and $Ti^{3+}$ and containing a moiety R, in the presence of a non-protic solvent to form a bicyclic intermediate having the structure

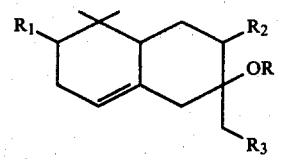

wherein R is a moiety derived from said reagent, and hydrolyzing under suitable conditions said intermediate to produce said bicyclic alcohol.

2. A method according to claim 1 wherein X is selected from the group consisting of iodo, chloro and bromo.

3. A method according to claim 1 wherein each of $R_1$, $R_2$ and $R_3$ are hydrogen.

4. A method according to claim 1 wherein $R_1$ is methyl and $R_2$ and $R_3$ are hydrogen.

5. A method of preparing a bicyclic alcohol having the structure

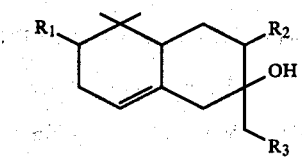

wherein $R_1$, $R_2$ and $R_3$ are hydrogen or methyl which comprises preparing a halogen-containing cyclohexane having the structure

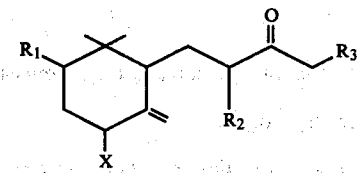

wherein X is a halogen by reacting under suitable conditions a substituted cyclohexene having the structure

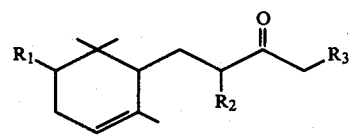

with a hypohalous acid having the formula HO—X, and converting said halogen-containing cyclohexane to said bicyclic alcohol in accordance with the process of claim 1.

6. A method of preparing a bicyclic alcohol having the structure

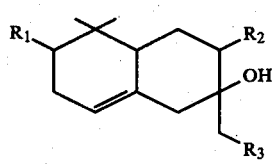

wherein each of $R_1$, $R_2$ and $R_3$ are hydrogen or methyl which comprises reacting under suitable conditions a halogen-containing cyclohexane having the structure

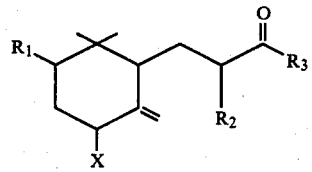

wherein each of $R_1$, $R_2$ and $R_3$ are hydrogen or methyl and X is a halogen with a reagent capable of effecting intramolecular cyclization of said halogen-containing cyclohexane compound and selected from the group consisting of metals from Groups 1 and 2 of the Periodic Table; electron transfer reagents such as Na/napthalene; alloys including amalgams of Group 1, 2 and 3 elements; Transition metals such as Fe, Cu, Cd and Hg; salts of elements of Groups 1, 2 and 3 of the Periodic Table; and salts of Transitions metals such as $Zn^{2+}$, $Cu^{2+}$, $Hg^{2+}$, $Cr^{2+}$, $V^{2+}$ and $Ti^{3+}$, in the presence of a protic solvent to produce said bicyclic alcohol.

7. A method according to claim 6 wherein X is selected from the group consisting of iodo, chloro and bromo.

8. A method according to claim 6 wherein each of $R_1$, $R_2$ and $R_3$ are hydrogen.

9. A method according to claim 6 wherein $R_1$ is methyl, and $R_2$ and $R_3$ are hydrogen.

10. A method of preparing a bicyclic alcohol having the structure

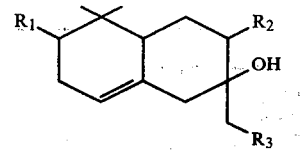

wherein $R_1$, $R_2$ and $R_3$ are hydrogen or methyl which comprises preparing a halogen-containing cyclohexane having the structure

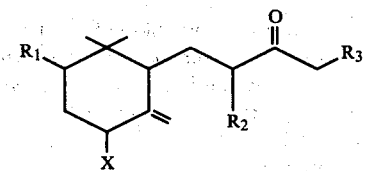

wherein X is a halogen by reacting under suitable conditions a substituted cyclohexene having the structure

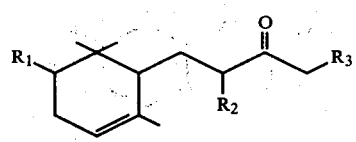

with a hypohalous acid having the formula HO—X, and converting said halogen-containing cyclohexane to said bicyclic alcohol in accordance with the process of claim 6.

* * * * *

UNITED STATES PATENT AND TRADEMARK OFFICE
CERTIFICATE OF CORRECTION

PATENT NO. : 4,341,908

DATED : July 27, 1982

INVENTOR(S) : Brian J. Willis et al

It is certified that error appears in the above-identified patent and that said Letters Patent are hereby corrected as shown below:

Column 8, the formula appearing under EXAMPLE 5 should correctly read:

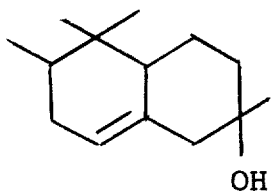

OH

Signed and Sealed this

Twenty-second Day of February 1983

[SEAL]

Attest:

GERALD J. MOSSINGHOFF

Attesting Officer

Commissioner of Patents and Trademarks